United States Patent
Chidambaram et al.

(10) Patent No.: US 6,593,499 B2
(45) Date of Patent: Jul. 15, 2003

(54) PROCESS FOR THE PREPARATION OF PHENYL KETONES

(75) Inventors: Mandan Chidambaram, Pune (IN); Chithravel Venkatesan, Pune (IN); Anand Pal Singh, Pune (IN); Arumugamangalam Venkataraman Ramaswamy, Pune (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 09/942,261

(22) Filed: Aug. 29, 2001

(65) Prior Publication Data

US 2003/0073870 A1 Apr. 17, 2003

(51) Int. Cl.[7] ................................................ C07C 45/46
(52) U.S. Cl. ........................ 568/314; 568/316; 568/319; 568/321
(58) Field of Search ................................ 568/314, 316, 568/319, 321

(56) References Cited

U.S. PATENT DOCUMENTS 4,714,781 A * 12/1987 Gupta
5,581,011 A * 12/1996 D'Ambra
6,184,418 B1 * 2/2001 Dubac et al.

OTHER PUBLICATIONS

Tanigaki, T. "Biphenyl Compounds" (1984) Chemical Abstracts 101:230145.
Walczak, A., et al. "Preparation of 4–Phenylbenzophenone". Przedsiebiorstwo–Farmaceutyczne "Jelfa" SA, Pol. (1997) Chemical Abstracts 126:263931.
Calvert, C. "Environmentally Friendly Catalysis Using Non-toxic Supported Reagents". (1992) Chemical Abstract 118:83211.
Zhang, L., et al. "Synthesis of Antifungal Bifonazole". (1992). Chemical Abstracts 117:233920.
Ullmann's Encyclopedia vol. A–1, (1981) p. 209.
Encyclopedia of Chemical Technology, vol. 11 (1944) p. 1055.
Friedel Crafts and Related Reaction, vol. III, Part 1 (1964) p. 62.
Gore, Peter H. "Aromatic Ketone Synthesis" pp. 234–237 (1981).

* cited by examiner

Primary Examiner—Johann Richter
Assistant Examiner—Sikarl A. Witherspoon
(74) Attorney, Agent, or Firm—Ladas & Parry

(57) ABSTRACT

The present invention relates to a process for the preparation of phenyl ketones of formula-I,

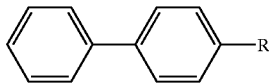

Formula-I Wherein R represents —$COCH_3$, —$COC_2H_5$ or —$COC_6H_5$, which comprises acylating the biphenyl with an acylating agent in an organic solvent in the presence of a solid crystalline microporous calalyst composite material.

2 Claims, No Drawings

PROCESS FOR THE PREPARATION OF PHENYL KETONES

The present invention relates to an improved process for the preparation of phenyl ketones. More particularly it relates to the said process for preparation of phenyl ketones having formula (I) by reacting biphenyl with the corresponding acylating agent over a solid acid catalyst.

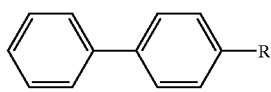

Formula-I

Where in R=—$COCH_3$ or —$COCH_2CH_3$ or —$COC_6H_5$.

Ketones are used mainly as a photo initiator for special printing plates, as well as for organic synthesis. Phenyl acetophenone and phenyl benzophenone are mainly used as pharmaceutical (antifungal) intermediate [Zhongguo Yiyao Gongye Zazhi, 23(3), 100–1 (Chinese) 1992.]; [Walczak, Antoni; Rzasa, Jozef; Labus, Stefan (PrzedsiebiorstwoFarmaceutyczne "jelfa" Sa, Pol.). Pol. PL 170632 B1 Jan. 31, 1997, 3pp. (Poland)].

In the prior art, an acyl group is introduced in the aromatic nucleus by an acylating agent such as an acyl halide, or itself in the presence of homogenous catalyst such as $AlCl_3$ or $BF_3$ (Encyclopedia of chemical Technology, Vol-II, page 1055, 1944)

Other process includes Friedel crafts acylation of various aromatics with a wide variety of acylating agents and metal halides such as $AlBr_3$, $FeCl_3$, $FeBr_3$, $SbCl_5$, $SbBr_3$, $TiCl_4$, $CbCl_5$, $NbCl_5$, $GaCl_3$ and $ZrCl_4$. Some of these may give yields comparable to those obtained with $AlCl_3$ (Friedel Crafts and Related reaction, Vol-111, Part-1, page-62, 1964, Ed. G. A. Olah).

Ortho- and para-acylated products of biphenyl have been made from the direct reaction of biphenyl with acylating agent or by the Fries rearrangement of aryl esters using Lewis acid catalyst, $AlCl_3$ (Ullmanns Encyclopedia Vol. A-1, p. 209); Calvert, Carys (Contract Chem. Ltd., Prescot/ Merseyside L34 9HY, UK). Symp. Pap.—Inst. Chem. Eng., North West. Branch, 3 (3, Integr. Pollut. Control Clean Technol.), 4.1–4.16 (English) 1992.

In one method propionylation of biphenyl with propionyl choloride was carried out using $ZnCl_2$ which consist of 12% yield of 4-Phenylpiophenone (4-PPP) (Friedel carft Related reaction Vol-III, part-1, 1964, Ed G. A. Olah).

A method comparising reacting biphenyl with propionyl chloride in the presence of $AlCl_3$ gives 65% yield of 4-PPP (Friedel carfts Related reaction Vol-III, part-1, 1964, Ed G. A. Olah)

Other process includes the preparation of 4-phenylbenzophenones (4-PBP) 74% by the benzolylation of biphenyl with $AlCl_3$ using $CHCl_3$ at room temperature. [Zhongguo Yiyao Gongye Zazhi, 23(3), 100–1 (Chinese) 1992.]; [Walczak, Antoni; Rzasa, Jozef; Labus, Stefan (PrzedsiebiorstwoFarmaceutyczne "jelfa" Sa, Pol.). Pol. PL 170632 B1 31 Jan. 31, 1997, 3 pp. (Poland)].

There have been known a number of methods for preparing phenyl ketones by reacting biphenyl with acetyl chloride, propionylchloride and benzoyl chloride respectively using Lewis acid catalysts. However the above methods are disadvantageous from the industrial point of view, because of low selectivity for 4-phenyl acetophenone, 4-phenyl propiophenone and 4-phenyl benzophenone and the catalyst used are homogeneous. Thus the large amount of base is required to neutralise the homogeneous catalysts.

The chemical industries are facing increasing pressure to reduce its impact on environment. This is particularly true in the production of phenyl ketones. Such reactions often require large quantities of minerals or Lewis acid catalysts which are destroyed or diluted during the aqueous work-up procedures, leadings to problems with equipment corrosion and expensive to treat. Furthermore, the reactions frequently use excess of reagents and are notoriously unselective. The overall result is excessive energy consumption, wastage of large quantities of Lewis acid catalysts and excessive impact on the environment. An additional major handicap of the homogeneous Lewis acid catalysts is the difficulty of their disposal, after use in the acetylation, propionylation and benzoylation reactions of biphenyl in an environmentally acceptable manner.

1. In view of the above mentioned drawbacks of homogeneous catalysts in the prior art process, it was found desirable during the course of the research work leading to the present invention to develop an environmentally acceptable solid selective, regenerable and recyclable zeolite catalysts for the production of biphenyl ketones and particularly 4-phenyl acetophenone, 4-phenyl propiophenone and 4-phenyl benzophenone in high selectivity from the acylation (acetylation, propionylation and benzoylation) of biphenyl with acetyl chloride, propionyl chloride and benzoyl chloride respectively, in the presence of solid acid catalyst composite materials alumino-silicate zeolite catalyst.

2. The $AlCl_3$ catalyst cannot be used with a number of hetrocyclic system which are decomposed by it due to its higher Lewis acid strength.

3. The use of $AlCl_3$ may give rise to some side reaction of intra-or intermolecular migration of alkyl groups, acylation and replacement of halogen atoms.

4. Difficult operational problem of corrosion.

5. Difficulty in the catalyst $AlCl_3$ or HCl removal from the products.

6. Use of stoichiometric amount of catalyst in all the methods described above. Some of them are hazardous and difficult to handle. In some cases catalyst is consumed during the reaction and in some cases catalyst are less selective.

It is therefore an object of the present invention to provide an improved process for the production of phenyl ketones by the acylation (acetylation, propionylation and benzoylation) of biphenyl in the presence of zeolite catalyst.

Another object of the present invention is to obviate the drawbacks and limitations of the prior art such as removal of HCl from the product form during the reaction, use of $AlCl_3$ give rise to many side chain reaction.

Still another object of the present invention is to provide an improved process which makes use of non-hazardous solid zeolite catalyst.

A further object of the present invention is to provide an improved process which leads to high yields of ketones and selectivity to para products resulting from high conversion of biphenyl and to provide an improved process which is safe not being prone to explosion.

The objects of the present invention are achieved by using microporous aluminosilicate zeolites as catalyst. In accordance with the process of the present invention biphenyl can be converted to 2-phenylacetophenone, 4-phenylacetophenone, 2-phenylpropiophenone, 4-phenylpropiophenone, 2-phenylbenzophenone and 4-phenylbenzophenone in the presence of a zeolite catalyst composite material aluminosilicate using solution of an acylating agent and biphenyl with stirring in an oil bath, such zeolites may be containing usually sodium or potassium but may further include other cations such as rare earth metals. The cations may be of the same type or of two or more different types.

Accordingly, the present invention provides a process for the preparation of phenyl ketones of formula-I,

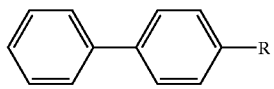

Formula-I

Wherein R represents —COCH$_3$, —COC$_2$H$_5$ or —COC$_6$H$_5$, which comprises acylating the biphenyl with an acylating agent in an organic solvent in the presence of a solid crystalline microporous catalyst composite material wherein the molar ratio of biphenyl to acylating agent is 1:1 at a temperature in the range of 50–200° C. for a period of about 20 hrs. and separating the desired product by conventional methods like gas-chromatography to obtain the desired product.

In one of the embodiment of the present invention, the acylating agent used is selected from the chlorides of acetic, propionic or benzoic acids.

In yet another embodiment of this invention the zeolite catalyst used in the reaction is selected from H-beta, H-Y, H-Mordenite, H-ZSM-5, RE-Y having molar composition in anhydrous state M/n:AlO$_2$:zSiO$_2$ (where M is proton or alkali or rare earth metals with valency n, and z is between 2–500) having SiO$_2$/Al$_2$O$_3$ molar ratio of from 2–50 having a pore size of 5–10 A°.

In still another embodiment the organic solvent used is nitrobenzene.

The process of the present invention is that, it does not pose any risk of explosion.

Thus, the process of the present invention is effectively and efficiently acylate the para-position of the substrate while suppressing the acylation at the ortho and meta position.

The present invention is described in a further detail with reference to the following examples, which should not be, however constructed to limit the present invention in any manner whatsoever.

EXAMPLE-1

This example illustrates the procedure for the preparation of a typical aluminosilicate crystalline material H-beta (Si/Al=13) [Na$_{0.92}$K$_{0.62}$(TEA)$_{7.6}$[Al$_{4.53}$Si$_{59.47}$O$_{128=}$] using tetraethylammoniumhydroxide (TEAOH) as a template. A mixture of water, TEAOH (40%), sodium hydroxide, potassium hydroxide solution was stirred until homogenized. Weighed amount of Fumed SiO$_2$ was added to the above solution and stirred until homogenized. Then weighed quantity of alumina source (Aluminium sulphate) was added and checked for pH~12. The solution after stirring for 2 h was kept at 413 K for 5 days in stainless steel autoclave. The crystalline material was filtered and dried at 373 K for 12 h and calcined at 713 K for 16 h in presence of air. The resulting sample was then exchanged 3 times with ammonium nitrate solution, filtered, washed with distilled water and then dried. The final dried sample was again calcined to obtain its protonic form with the flowing of air at 713 K for 12 h. Crystallinity of the sample has been checked with XRD and compared with the standard XRD pattern of the corresponding zeolite (H-beta) material.

EXAMPLE-2

This example illustrates the procedure and effect of reaction time on the acetylation of biphenyl to 4-phenylacetophenone (4-PAP), 2-phenylacetophenone (2-PAP). 1.54 g (10 mmol) of biphenyl, 1.4 g (10 mmol) of acetyl chloride and 20 ml of nitro benzene (as solvent) were taken in a two necked round bottom flask. 0.5 g of catalyst composite material zeolite H-beta was added in the reaction mixture. The reaction mixture was heated up to 443 K with stirring. The reaction was continued for 9 h. The reaction mixture was cooled down to room temperature and analyzed with gas chromatograph. The results are recorded in Table 2.

TABLE 2

Acetylation of biphenyl with acetyl chloride over catalyst composite materials zeolite H-Beta after 9 h.

| Reaction time (h) | 1 | 3 | 6 | 9 |
|---|---|---|---|---|
| Conversion of biphenyl (wt %) | 0.9 | 6.8 | 7.2 | 9.2 |
| Product distribution (wt %) | | | | |
| 4-phenylacetophenone (4-PAP) | 100 | 98.8 | 90.5 | 70.8 |
| 2-phenylacetophenone (2-PAP) | 0 | 1.2 | 9.5 | 29.2 |
| 4-PAP/2-PAP | 0 | 82.3 | 9.5 | 2.4 |

EXAMPLE-3

This example illustrates the procedure and effect of reaction time of the propionylation of biphenyl to 4-phenylpropiophenone (4-PPP) and 2-phenylpropiophenone (2-PPP). 1.54 g of biphenyl, 1.4 g of propionylchloride and 20 ml of nitrobenzene (as solvent) were taken in a two necked round bottom flask in an oil bath. 0.5 g of catalyst composite material zeolite H-beta was added to the reaction mixture. The reaction mixture was heated up to 443 K with stirring and the reaction was continued for 9 h. The reaction mixture was cool down to room temperature and the products are analyzed by gas chromatograph. The results are reported in Table 3.

TABLE 3

Propionylation of biphenyl with propionyl chloride over catalyst composite materials zeolite H-beta after 9 h.

| Reaction time (h) | 1 | 3 | 6 | 9 |
|---|---|---|---|---|
| Conversion of biphenyl (wt %) | 7.9 | 9.1 | 10.1 | 8.2 |
| Product distribution (wt %) | | | | |
| 4-phenylpropiophenone (4-PPP) | 83.0 | 78.0 | 76.0 | 72.0 |
| 2-phenylpropiophenone (2-PPP) | 17.0 | 22.0 | 24.0 | 28.0 |
| 4-PPP/2-PPP | 4.8 | 3.5 | 3.1 | 2.5 |

EXAMPLE-4

This example illustrates the procedure and effect of reaction time on the benzoylation of biphenyl to 4-phenylbenzophenone (4-PBP) and 2-phenylbenzophenone (2-PBP). 1.54 g of biphenyl, 1.4 g of benzoylchloride and 20 ml of nitrobenzene (as solvent) were taken in a two-necked round bottom flask in an oil bath, 0.5 g of catalyst composite material zeolite H-beta was added to the reaction mixture. The reaction mixture was heated up to 443 K with stirring and the reaction was continued for 9 h, and cooled down to room temperature and analyzed by gas chromatography. The results are recorded in table 4.

TABLE 4

Benzoylation of biphenyl with benzoylchloride over catalyst composite materials zeolite H-beta after 9.

| Reaction time (h) | 1 | 3 | 6 | 9 |
|---|---|---|---|---|
| Conversion of biphenyl (wt %) | 17.6 | 20.0 | 24.5 | 40.0 |
| Product distribution (wt %) | | | | |
| 4-phenylbenzophenone (4-PBP) | 97.0 | 96.0 | 97.0 | 97.0 |
| 2-phenylbenzophenone (2-PBP) | 3.0 | 4.0 | 3.0 | 3.0 |
| 4-PBP/2-PBP | 32.0 | 24.0 | 32.0 | 32.0 |

EXAMPLE-5

This example illustrates the procedure for the benzoylation of biphenyl to 4-phenylbenzophenone (4-PBP) and 2-phenylbenzophenone (2-PBP). 1.54 g (10 mmol) of biphenyl, 1.4 g (10 mmol) of benzoyl chloride and 20 ml of nitrobenzene (as solvent) were taken in a two necked round bottom flask. 0.5 gm of catalyst composite material zeolite H-beta was added in the reaction mixture. The reaction mixture was heated upto 443 K with stirring. The reaction was continued for 6 h. The reaction mixture was cooled down to room temperature and analysed with gas chromatograph. The results are recorded in Table 5.

TABLE 5

Benzoylation of biphenyl with benzoylchloride over catalyst composite material, aluminosilicate, Zeolite H-beta, after 6 h.

| Reaction time (h) | 6 |
|---|---|
| Conversion of biphenyl (wt %) | 24.5 |
| Product distribution (wt %) | — |
| 4-phenylbenzophenone (4-PBP) | 97.1 |
| 2-phenylbenzophenone (2-PBP) | 2.9 |
| 4-PBP/2-PBP | 33.8 |

EXAMPLE-6

This example illustrates the procedure for the benzoylation of biphenyl to 4-phenylbenzophenone (4-PBP) and 2-phenylbenzophenone (2-PBP). 1.54 g (10 mmol) of biphenyl, 1.4 g (10 mmol) of benzoyl chloride and 20 ml of nitrobenzene (as solvent) were taken in a two necked round bottom flask. 0.5 gm of catalyst composite material zeolite H-Y was added in the reaction mixture. The reaction mixture was heated upto 443 K with stirring. The reaction was continued for 6 h. The reaction mixture was cooled down to room temperature and analysed with gas chromotograph. The results are recorded in Table 6.

TABLE 6

Benzoylation of biphenyl with benzoylchloride over catalyst composite material, aluminosilicate, Zeolite H—Y, after 6 h.

| Reaction time (h) | 6 |
|---|---|
| Conversion of biphenyl (wt %) | 2.6 |
| Product distribution (wt %) | — |
| 4-phenylbenzoophenone (4-PBP) | 80.0 |
| 2-phenylbenzophenone (2-PBP) | 20.0 |
| 4-PBP/2-PBP | 4.0 |

EXAMPLE-7

This example illustrates the procedure for the benzoylation of biphenyl to 4-phenylbenzophenone (4-PBP) and 2-phenylbenzophenone (2-PBP). 1.54 g (10 mmol) of biphenyl, 1.4 g (10 mmol) of benzoyl chloride and 20 ml of nitrobenzene (as solvent) were taken in a two necked round bottom flask. 0.5 gm of catalyst composite material zeolite H-mordenite was added in the reaction mixture. The reaction mixture was heated upto 443 K with stirring. The reaction was continued for 6 h. The reaction mixture was cooled down to room temperature and analysed with gas chromotograph. The results are recorded in Table 7.

TABLE 7

Benzoylation of biphenyl with benzoylchloride over catalyst composite material, aluminosilicate, Zeolite H— mordenite, after 6 h.

| Reaction time (h) | 6 |
|---|---|
| Conversion of biphenyl (wt %) | 1.7 |
| Product distribution (wt %) | — |
| 4-phenylbenzoophenone (4-PBP) | 91.1 |
| 2-phenylbenzophenone (2-PBP) | 8.6 |
| 4-PBP/2-PBP | 10.6 |

EXAMPLE-8

This example illustrates the procedure for the benzoylation of biphenyl to 4-phenylbenzophenone (4-PBP) and 2-phenylbenzophenone (2-PBP). 1.54 g (10 mmol) of biphenyl, 1.4 g (10 mmol) of benzoyl chloride and 20 ml of nitrobenzene (as solvent) were taken in a two necked round bottom flask. 0.5 g of catalyst composite material zeolite H-ZSM-5 was added in the reaction mixture. The reaction mixture was heated upto 443 K with stirring. The reaction was continued for 6 h. The reaction mixture was cooled down to room temperature and analysed with gas chromotograph. The results are recorded in Table 8.

TABLE 8

Benzoylation of biphenyl with benzoylchloride over catalyst composite material, aluminosilicate, Zeolite H— ZSM-5, after 6 h.

| Reaction time (h) | 6 |
|---|---|
| Conversion of biphenyl (wt %) | 4.8 |
| Product distribution (wt %) | — |
| 4-phenylbenzoophenone (4-PBP) | 90.0 |
| 2-phenylbenzophenone (2-PBP) | 10.0 |
| 4-PBP/2-PBP | 9.0 |

EXAMPLE-9

This example illustrates the procedure for the benzoylation of biphenyl to 4-phenylbenzophenone (4-PBP) and 2-phenylbenzophenone (2-PBP). 1.54 g (10 mmol) of biphenyl, 1.4 g (10 mmol) of benzoyl chloride and 20 ml of nitrobenzene (as solvent) were taken in a two necked round bottom flask. 0.5 g of catalyst composite material zeolite RE-Y was added in the reaction mixture. The reaction mixture was heated upto 443 K with stirring. The reaction was continued for 6 h. The reaction mixture was cooled down to room temperature and analysed with gas chromotograph. The results are recorded in Table 9.

TABLE 9

Benzoylation of biphenyl with benzoylchloride over catalyst composite material, alunilnosilicate, Zeolite RE—Y, after 6 h.

| Reaction time (h) | 6 |
|---|---|
| Conversion of biphenyl (wt %) | 2.4 |
| Product distribution (wt %) | — |
| 4-phenylbenzoophenone (4-PBP) | 84.0 |
| 2-phenylbenzophenone (2-PBP) | 16.0 |
| 4-PBP/2-PBP | 5.3 |

The process of present invention shows remarkably high industrial merits over prior art process for the preparation of 4-phenylacetophenone, 4-phenylpropiophenone and 4-phenylbenzophenone in high selectivity.

The starting materials are easily available and easy to handle and that ketone can be produced in high yield by extremely simple operation.

Yet another important and advantageous feature of the process of the present invention is the use of the non-hazardous solid alumino silicate catalysts.

Another important and advantageous feature of the process of the present invention is that it does not pose risk of explosion. The most important and advantageous feature of the process of the invention is that both the yield and selectivities to para-subsitituted phenyl ketones are very high.

The use of zeolite as the catalyst in the liquid phase organic reaction of the present invention provides the following advantages:

1. Easy separation of the product from the solid by means of a simple procedure of filtration.
2. Adsorption or inclusion of substrate and reagent molecules into the small pores of solids with nanometer dimension organizes in the molecules in close proximity to lower the activation energy of the reaction.
3. Well defined crystalline structure, uniform micro cavities effecting selective reactions of organic molecules incorporated therein under restriction.
4. High cation-exchangeability to unsure easy adjustment of their acidic and basic properties in a wide range of acidity.

We claim:

1. A process for the preparation of a phenyl ketone of formula-I

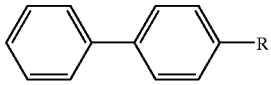

Formula-I wherein R represents $COCH_3$, $COC_2H_5$, or $COC_6H_5$ which comprises acylating a biphenyl with an acylating agent wherein the molar ratio of biphenyl to acylating agent is 1:1, the acylating agent is selected from the group consisting of acetyl chloride, proopionyl chloride, benzoyl chloride and mixtures thereof, in nitrobenzene in the presence of a solid crystalline microporous catalyst composite material wherein the catalyst is selected from the group consisting of H-beta, H-Y, H-Mordenite, and mixtures thereof at a temperature in the range 50–2000° C. for a period of up to 9 hours and separating using gas-chromatography to obtain the phenyl ketone of Formula I.

2. A process as claimed in claim 1 wherein said catalyst is H-beta.

* * * * *